United States Patent [19]

Mikkelsen

[11] Plant 5,126

[45] Oct. 25, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,077

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Columbia and characterized by its excellent keeping qualities; generally light pink flower color; firm, thick and non-fragile flower petal texture; relatively slow growth and compact, tight habit; early flowering response; dark green foliage which provides a pleasant contrast with flower color; best performance under full sunlight, and its adaptability to different environments of use, including use initially as a house plant which can later be transferred to the garden.

1 Drawing Figure

The present invention relates to a new and distinctive cultivar of Impatiens plant known by the cultivar name Columbia. The new cultivar is botanically known as Impatiens, and was developed by me through controlled breeding in Ashtabula, Ohio. The seed parent was 77-684-1 (Mikkelsen) and the pollen parent was 78-800-8 (Mikkelsen). Asexual reproduction of terminal or stem cuttings has shown that the unique features of this new impatiens are stabilized and are reproduced true to type in successive propagations.

The following characteristics distinguish Columbia from both its parent varieties and other cultivated impatiens of this type known and used in the floriculture industry:

1. Columbia has remarkable flower keeping qualities for a New Guinea Impatiens. It will be noted in the photograph that the older flowers are below the terminal swirl of buds and have retained their excellent color and quality.

2. Flower color is a light pink shade which differs from other patented and known New Guinea Impatiens. The flower petal texture is firm, thick, and less fragile, which adds to keeping qualities. This new quality of petal texture will be of great importance in hybridizing New Guinea Impatiens for house plant purposes.

3. Flower size is medium to large for New Guinea Impatiens, being 5 to 6 cm. in diameter. Flower color in contrast to foliage is more attractive than the contrast in Telstar, disclosed in U.S. Plant Pat. No. 4,733.

4. The new cultivar tends to be slow growing and not as full a plant as compared to most of the Mikkelsen hybrids. The plant is short and compact, not as loose or large as Telstar.

5. Flowering response is very early, often presenting problems of obtaining vegetative cuttings for propagation. Early budded cuttings allow for propagation of stem cuttings for quick production of small flowering plants for early spring sales.

6. Foliage is dark green with some mid-rib basal variegation when plants are grown in full sunlight.

7. The new cultivar does best in full sunlight to slightly screened light. Flower color intensifies slightly under screened light but flower quantity is noticably reduced in shaded areas.

8. Improved flower and foliage qualities allow the cultivar to be sold for multi-use, that is, a houseplant which can be later transferred outside for garden use.

9. The new cultivar can be produced as a small potted plant, hanging basket, mass display in garden plantings, or, as illustrated, as a single specimen accent plant. Flowering continued outside in Ashtabula, Ohio until end of October with first frost below −1.5° C.

10. Unlike Sultana Impatiens, Mikkelsen New Guinea Impatiens hybrids require high light and ample fertility for maximum expression of characteristics.

The accompanying colored photograph taken in mid-September outdoors illustrates the overall appearance of Columbia. The photo is a generally top perspective view of the plant and shows the colors as true as it is reasonably possible to obtain in a colored reproduction of this type.

The following is a detailed description of my new impatiens cultivar based on plants produced under commercial practices in Ashtabula, Ohio. The illustrated specimen was planted outside the first week of June from a 4" pot. By early September the plant measured 45 cm. diameter and 25 cm. high. Color references are made to The Royal Horticultural Society Color Chart except where general terms of ordinary dictionary significance are used.

Parentage: Controlled cross of Mikkelsen seedling 77-684-1 × Mikkelsen seedling 78-800-8.

Propagation:

(A) *Stem cuttings.*—Cutting 15 mm. long will develop to 4–5 cm. in 21–28 days.

(B) *Time to initiate roots.*—8–10 days at 23° C. summer.

(C) *Time to initiate roots.*—12–14 days at 20° C. winter.

Plant description:

(A) *Form.*—Symmetrically rounded plant with rigid semi-upright stems, close to medium internodes, self-branching, early flowering herb. Light red stems.

(B) *Habit of growth.*—Medium slow growing self branching, low symmetrical bush type growth.

(C) *Foliage.*—Leaves simple, opposite on vegetative shoots but in a whorl placement when flowering. New foliage and flowering continue simultaneously as plant growth advances. (1) Size: Average leaf at maturity 7–8 cm. long × 2.5–3 cm. wide. (2) Shape: Lanceolate, apex very acuminate, base acute. (3) Texture: Top side rugose, underside glabrous. (4) Margin: Entire, finely ciliate. (5) Color: Young foliage, top side yellow green 146-A; under side yellow green 147-B. Mature foliage, top side darker than yellow green 147-A; under side yellow green 147-B. Some yellow variegation at base of leaf grown in high light. (6) Venation: pinnate.

Flowering description:

(A) *Flowering habits.*—Indeterminate, early, and continuous flowering year around in Ohio.

(B) *Natural flowering season.*—Indeterminant.

(C) *Flower buds.*—Ellipsoidal, flowers perfect, 5 cm. long red spur with throat originating from sepal.

(D) *Flowers borne.*—Individually on pedicel from whorl of 6–8 buds.

(E) *Quantity of flowers.*—Number of buds per whorl is average for New Guinea Impatiens hybrids of this type. Size of flowers and keeping qualities give impression of prolific flowering.

(F) *Petals.*—(1) Shape: Top petal dominant, all petals heart-shaped, indented on apex. (2) Color: Top side in summer when opening, red purple 62-A, with dark center around ovary area, fading to red purple 62-C or lighter in periods of high temperature; under side, red purple 62-D toward very light pink. (3) Number of petals: Five (5), lower four nearly symmetrical. (4) Size of flowers: 5×6 cm. in diameter; petals are thick and firm.

(G) *Reproductive organs.*—(1) Stamens: Five (5) in number. (a) Anther shape: Hooded, color red to pink. (b) Pollen color: Cream. (2) Pistils: (a) Stigma: Five (5) in number, pointed star shape, colorless. (b) Style: Colorless. (c) Ovaries: Five (5) in number, celled; size, 5 mm. long before fertilization, green in color. Capsule explosively dehiscent.

Disease resistance: Since the origination of the cultivar in 1979, there has been no apparent problems with diseases or insects other than botrytis rot under adverse environments.

I claim:

1. A new and distinct cultivar of impatiens plant known by the cultivar name Columbia, as described and illustrated, and particularly characterized by its excellent keeping qualities; generally light pink flower color; firm, thick and non-fragile flower petal texture; relatively slow growth and compact, tight habit; early flowering response; dark green foliage which provides a pleasant contrast with flower color; performs best under full sunlight, and its adaptability to different environments of use, including use initially as house plant which can later be transferred to the garden.

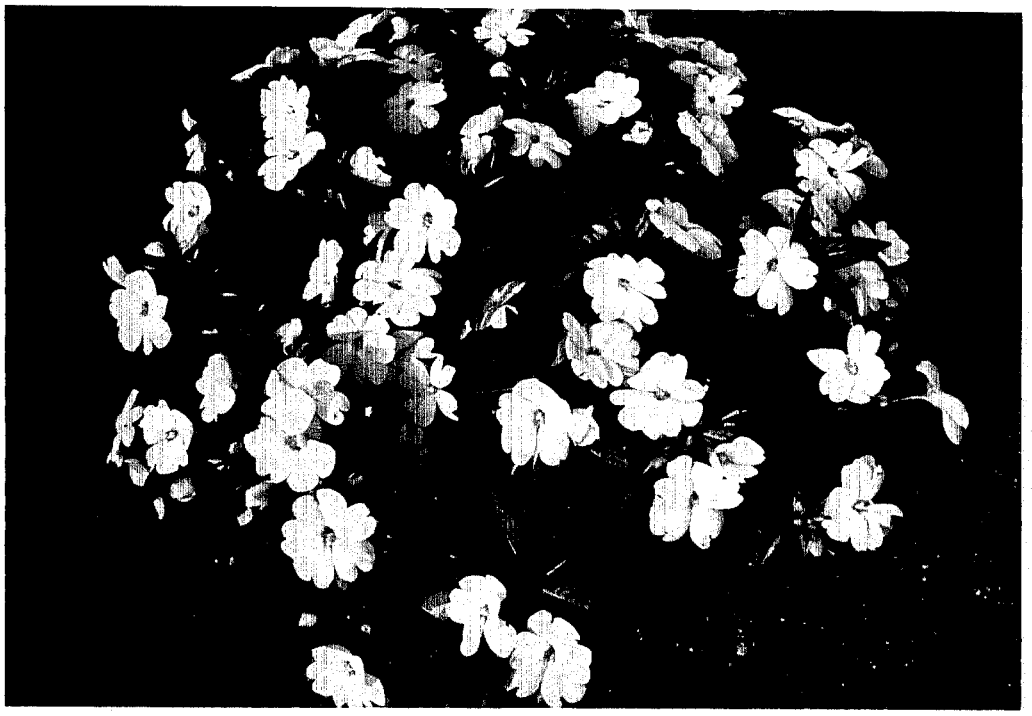

* * * * *